United States Patent [19]

Moore et al.

[11] Patent Number: 4,572,197
[45] Date of Patent: Feb. 25, 1986

[54] BODY HUGGING INSTRUMENTATION VEST HAVING RADIOACTIVE EMISSION DETECTION FOR EJECTION FRACTION

[75] Inventors: Richard H. Moore, Concord; H. William Strauss, Newton Centre; Nathaniel M. Alpert, Swampscott, all of Mass.

[73] Assignee: The General Hospital Corporation, Boston, Mass.

[21] Appl. No.: 616,491

[22] Filed: Jun. 1, 1984

Related U.S. Application Data

[63] Continuation-in-part of Ser. No. 394,465, Jul. 1, 1982.

[51] Int. Cl.⁴ ............................................. A61B 5/04
[52] U.S. Cl. ................................. 128/644; 128/659; 128/691; 128/721; 128/733; 128/736
[58] Field of Search ............... 128/644, 659, 691, 721, 128/733, 736

[56] References Cited

U.S. PATENT DOCUMENTS 3,534,727 10/1970 Roman ................................ 128/644

FOREIGN PATENT DOCUMENTS 274612 7/1951 Switzerland ...................... 128/644

Primary Examiner—Kyle L. Howell
Attorney, Agent, or Firm—Weingarten, Schurgin, Gagnebin & Hayes

[57] ABSTRACT

A vest for positioning medical instrumentation about the human or animal torso to provide ambulatory monitoring of patient cardiac functions or administration of medication or therapy with reasonable freedom of movement while maintaining precise positioning of the instrumentation relative to the torso. The vest functions to provide accurate placement of such instrumentation as a radioactive emission sensor for monitoring ejection fraction. The vest typically includes a sheet of a dimensionally rigid material such as a low density polymer tailored to fit between neck and hips and to surround the torso, terminating on the back. Straps are provided to fasten the sheet ends together at the back and to suspend it from the shoulders. The vest may also be instrumented to function as a transducer itself to detect chest expansion for heart beat or lung volume monitoring.

24 Claims, 7 Drawing Figures

BODY HUGGING INSTRUMENTATION VEST HAVING RADIOACTIVE EMISSION DETECTION FOR EJECTION FRACTION

CROSS REFERENCE TO RELATED APPLICATION

This application is a continuation-in-part of our copending application, Ser. No. 394,465, filed July 1, 1982 incorporated herein by reference.

The invention herein was made in the course of work under Grant No. HL24623 from the Department of Health and Human Services.

The detection of many cardiac malfunctions is impeded by the intermittent occurrence of such malfunctions. They may appear only occasionally, masking detection during clinical observation or examination. In other situations it is desirable to be able to monitor heart functioning during normal or near normal subject activity in order to accumulate information on the functioning of the heart in normal and diverse stress situations. Also, in many cases, it is desired to administer medication or therapy to the body during ambulatory conditions.

A portable system capable of being easily placed about the human torso so as to permit a subject under investigation to be monitored in cardiac function during normal or near normal daily activity is shown in our above-identified application. One parameter of interest during such studies and examinations is the cardiac ejection fraction or the relative volume of fluid pumped by the heart on each beat. This can be accomplished by applying a radioactive substance to the subject's blood so that it circulates through the heart, ultimately appearing in the left ventricle. A detector of the radioactive emissions is placed proximate to the heart and senses the level of radioactive decay. Since this is a function of the volume of blood in the left ventricle, the ejection fraction can be determined from the variations in the detected radioactivity over a heart beat cycle.

It is of substantial medical significance to be able to make such measurements while the subject is engaged in normal daily activity in order to detect infrequently occurring irregularities or to document this particular heart characteristic during a range of subject actions. In other cases it is desirable to administer medication or therapy to the subject over time while the subject is ambulatory. In order to avoid the introduction of errors into the measurements, or disturb the administration, it is important the detector or sensor, or applying instrumentation, be located in a position relative to the torso which will not vary significantly during normal subject activity. Any displacement of the detector or other instrumentation during monitoring can introduce a variation in the detected functioning that rendures the detected function, such as ejection fraction, suspect. A disturbance in the applying instrumentation can also result in undesired loss of application or application to wrong areas.

BRIEF SUMMARY

The present invention provides a vest adapted to be worn about the torso of a human or animal subject being monitored in heart or other organ function or being administered medication or therapy during ambulatory activities. In one exemplary use, the vest positions a detector for heart activity, such as a radioactivity detector, in a location relative to the heart that is kept constant during routine or even stressful activities of the subject.

The vest typically comprises a sheet of a low density, thermally formable plastic. The sheet is readily thermally formable to an approximate torso contour and can bend or flex to permit it to adjust to the torso of the subject. Strapping secures the sheet in this position allowing body motion, but restricting the motion of the front of the vest relative to the subject's torso. A detector for radioactivity is positioned and secured to the sheet at a location which places it over the subject's heart. The security of positioning of the vest insures that the motions the subject executes will not result in a variation of detector output attributable to those motions.

High voltage energizing circuitry for the detector is furthermore located in the detector assembly or on the vest proximate to the detector, eliminating lengthy and dangerous high voltage leads.

Detectors for other than heart function monitoring may be utilized including sonic or ultra sound, plethysmograph, temperature, ECG, EMG, skin resistance and wetness, or thermal loss. In some cases, such as ECG, EMG or temperature detection, an array of detectors may be utilized and affixed to the vest. The vest further permits fixed placement of broadcast and receiving units on opposite sides of body organs to be monitored, such as the use of microwave emitters and receivers, typically in arrays, to detect dielectric constants. The vest may itself be instrumented with strain gages or elastic elongation detectors to cause the vest to act as a transducer for heart beat detection, blood pressure or tidal lung volume measurement.

The vest will also function as a stable platform for instrumentation used to administer medications, as through infusion apparatus, or therapy, such as radiant heat, light or nuclear particles.

The sheet material forming the vest is typically dimensioned to extend vertically (or horizontally with animals) from a point just below the subject's neck to a point above the hips. Horizontally, the sheet is preformed thermally to wrap around the torso from the back of the subject, under one arm, across the breast, under the other arm to the back. Strapping secures the back ends together and loops over the shoulders, supporting the vest from the shoulders.

In order to minimize abrasion or chafing on the subject's skin from the edges of the sheet material of the vest, adhesive-backed thin padding is applied over the edges of the sheet and other chafe points as needed to prevent abrasion. A petroleum jelly lubricant is applied at potential abrasion sites where padding alone is inadequate. The sheet is preferably apertured to promote ventilation of the torso, allowing heat to exhaust, providing instrument mounting sites, and aiding vest flexing and formability.

DESCRIPTION OF THE DRAWING

The present invention will be more fully understood by reference to the solely description below and to the accompanying drawing of which.

DETAILED DESCRIPTION

The present invention contemplates a vest for positioning medical instrumentation about the torso of a human or animal subject in a manner that permits most routine motions of every day living but prevents the dislocation of the instrumentation relative to the position of an organ or tissue of interest within the torso.

Figure 1:
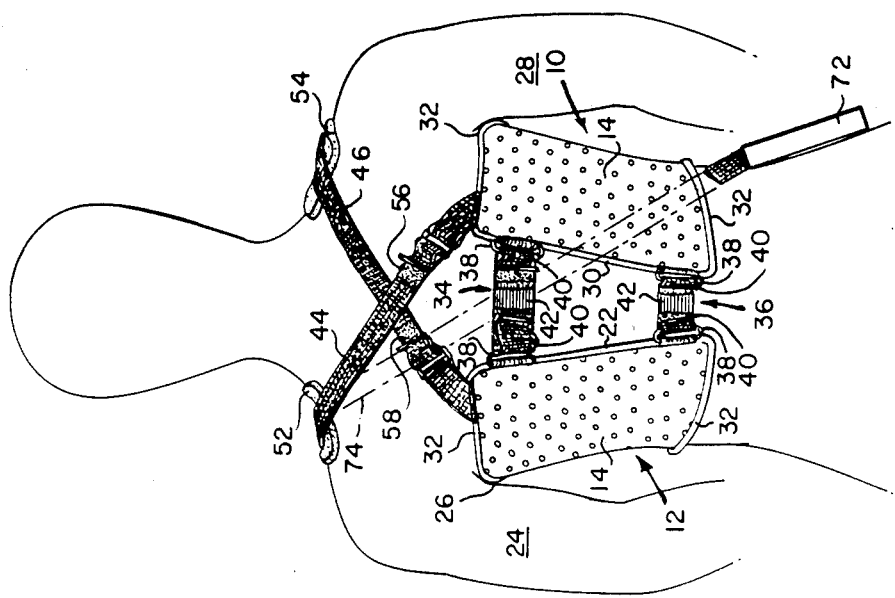
FIG. 1 is a front view of the vest of the present invention as worn by a subject.

By reference to FIG. 1 the structure of a vest according to the invention and its utilization is described. As shown there, a torso 10 is seen in front view and has wrapped around it a vest 12 comprising a sheet 14. The sheet 14 preferable comprises a plastic such as a low density ployethelyne in which the molecules are expanded in curing to impart thermal preformability, flexibility, and light weight to the vest structure. The sheet may also be apertured with holes 16 to further enhance formability, flexibility and reduce the weight, and to exhaust body heat for wearer comfort. The sheet thus formed is dimensionally rigid but flexible in its ability to bend around and contour to the torso 10.

Figure 2:
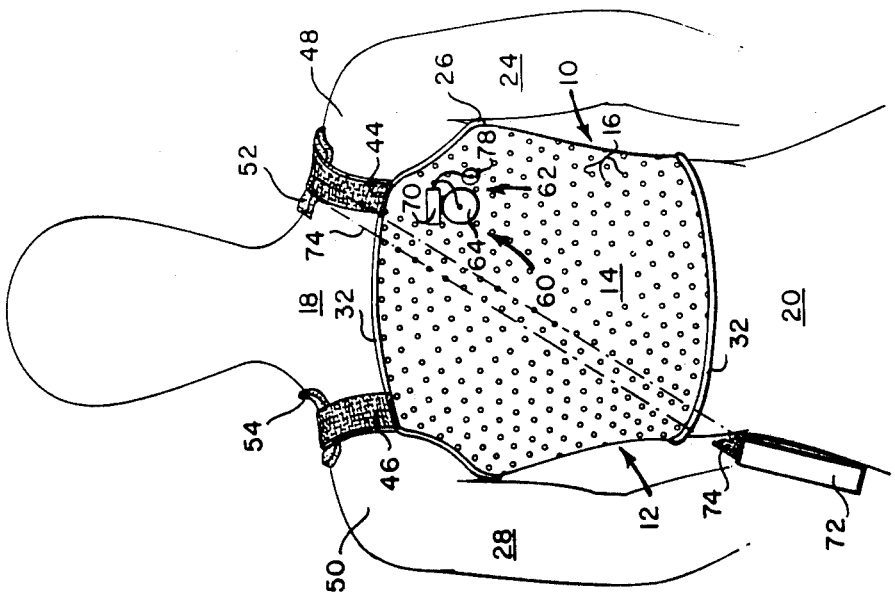
FIG. 2 is a back view of the vest shown in FIG. 1.

The sheet 14 is dimensioned to extend vertically from just below the neck 18 to a position above the hips 20. The sheet 14 extends horizontally around the torso from the back (FIG. 2) at a first end 22, under the arm 24, being cut low to accommodate the arm pit 26. The sheet then is adapted to cross the breast of the torso to pass under the other arm 28, being cut low to accommodate the other arm pit, terminating at an end 30 in the back. Peripheral portions of the sheet 14 are edged or covered with a soft material 32 such as an adhesive backed thin padding to reduce abrasion of the skin of the subject during use. Lubricants, typically petroleum jelly, can be added between sheet and skin in use.

Figure 3:
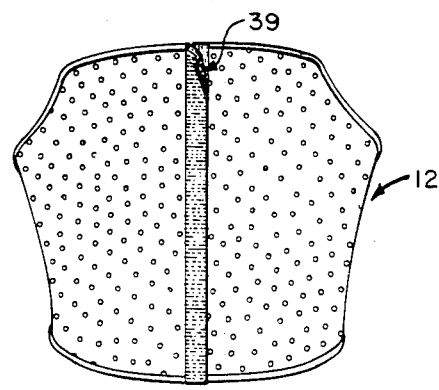
FIG. 3 shows a quick release modification to the vest of the present invention.

The ends 22 and 30 are held together in the rear or back portion by straps 34 and 36 which are passed through loops 38, fastened in the ends 22 and 30, and attach back upon themselves through hook and pile fasteners 40 such as VELCRO or other adjustable, releasable fasteners. The straps 34 and 36 may include elastic portions 42 to permit greater subject motion within the vest 12. Alternatively, the elastic or spring elements may be incorporated into the loops 38 or their manner of attachment to the sheet 14. The fasteners for the straps 34 and 36 are preferably such that they will unfasten if the subject inhales to extreme lung capacity. In any event, the strapping permits rapid removal of the fastenings and vest by attendants as may become necessary in an emergency. A modification to the vest front is shown in FIG. 3. A quick release strip 39, such as a hook and pile fastener, snaps, or zipper, extends vertically across the vest to permit instant vest release and removal.

Additional straps 44 and 46 are attached to the top front of the sheet 14 and loop over the shoulders 48 and 50, over pads 52 and 54 for comfort and protection. The straps 44 and 46 proceed over the shoulders and cross each other in the back extending through hook and pile or other quick release fasteners 56 and 58 to opposite ends 30 and 22 of the sheet 14.

In this manner the sheet is positioned over the torso 10 to allow subject flexibility but prevent the movement of the vest 12 relative to a location 60 to be instrumented. The sheet may be made available in a variety of sizes and shapes to fit all torso types. In addition, the sheet may be distored by heating to provide a closer fit with typical or individual torso topography. Also contributing to the fit of the vest, reducing relative motion between the torso and the vest, is a match in vest shape to the generally conical or ellipsoidal shape of the rib cage of the torso. The plastic material of the sheet 14 can be thermally deformed at low temperatures such as 140° F., to facilitate this match and other contouring. This match greatly enhances the ability of the vest 12 to move with the torso and thus follow its motions, avoiding measurement or application inaccuracy. In use, the vest has achieved repeated, accurate data acquisition over 6-8 hour intervals of ambulatory use without undue user discomfort.

In one application to the detection of heart ejection fraction, the front of the vest, at a location 62, is adapted to receive and secure by conventional means a detector module 64 for sensing radioactive emissions from blood in the heart. Holes 16 provide sites for such instrumentation attachment if desired. Typically, in the measurement of ejection fraction, the detector module 64 is placed over the left ventricle of the subject's heart. Heart position identification with a gamma camera may be useful in initial positioning of the vest relative to the heart left ventricle.

The detector module 64 typically has a sodium iodide crystal detector. Alternatively the detector module 64 includes a parallel array of cadmium telluride detectors as described in our copending application identified above, and specifically incorporated herein by reference.

A high voltage power supply 70 is provided for the detector and located proximate to or embodied within the detector module 64 to minimize the length of high voltage cabling between supply and detector. Electronics, as shown in our above identified application, is typically distributed between a hip module 72, supported about the shoulder by a strap 74, and the detector module 64. Electronics 72 powers the detector module 64 and provides signal processing as shown in the above identified application. The result of such signal processing is to permit determination of ejection fraction.

Associated with the detector module 64 is a background detector 78 which functions to monitor background radiation for normalizing the output of the main detector module 64 as noted in the above identified application.

Figure 4:
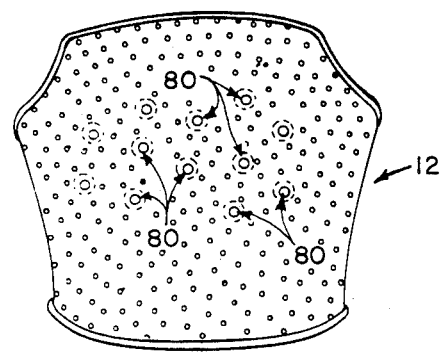
FIG. 4 shows the application of the vest to arrayed detectors, or emitters.

Alternative detectors for which the vest is particularly adapted include sensors for sound or ultra sound (including sectored or Doppler sensing) plethysmography, ECG, EMG, ratiographic tissue absorption characteristics, temperature distributions, skin resistance, skin wetness, and thermal loss measurement. The vest 12 is well adapted to positioning such sensors in an array 80, as shown in FIG. 4, in one or more areas of the vest.

Figure 5:
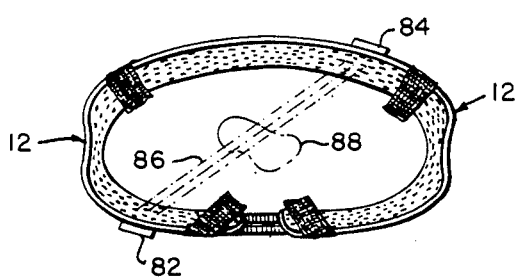
FIG. 5 shows the application of the vest to a through the body instrumentation function.

As shown in FIG. 5, the vest 12 is also adaptable to mount a broadcaster 82 and receiver 84 on opposite torso sides, and in particular to apply a radiation 86 through an organ 88 to detect organ function as by its radiation absorption. In one example an arrayed microwave emitter can be utilized opposite an arrayed microwave detector to determine organ dielectric properties from radiation absorption and re-radiation.

Figure 6:
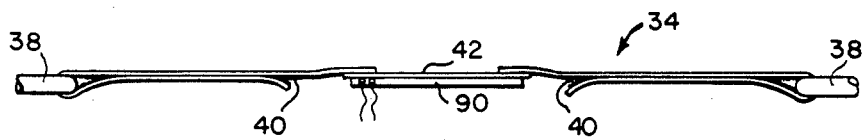
FIG. 6 shows instrumentation to the vest allowing its use as a transducer.

The vest will also function as a transducer itself if instrumented to detect its deflections under the pressure of heart pumping, or lung-chest expansion with respiration. A strain gage or similar sensor 90 can be affixed to the vest or to the strapping as shown in FIG. 6. Its output can be calibrated using independent heart beat, blood pressure, or spirometric detection permitting subsequent ambulatory monitoring of these functions.

The vest additionally functions to permit the attachment of instrumentation adapted to administer medication through infusion apparatus, or to permit continuous application of a therapeutic radiation. Such radiation can take the form of heat, light, or nuclear as desired. The vest also readily permits combining several monitoring or administration functions simultaneously.

Figure 7:
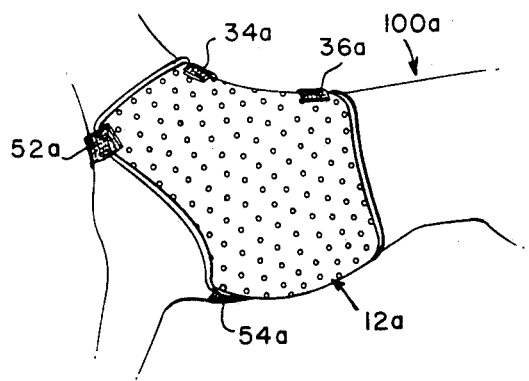
FIG. 7 shows the application of the vest to general animal use.

As shown in FIG. 7, a modified vest 12a, utilizing the stability imparting fastenings 34a, 36a, 52a, and 54a and contouring features noted above, is used to permit instrumentation of an animal 10a. Similar stability of instrument placement can be achieved with animals as well.

The above described vest provides a secure platform for medical monitoring of heart functions in an ambulatory subject. Changes can be implemented to the teaching without departing from the spirit of the invention. Accordingly, the invention is to be limited solely in accordance with the following claims.

What is claimed is:

1. A vest for positioning medical instrumentation about the human or animal torso in a fixed position relative to a torso located organ or tissue for ambulatory torso instrumentation, said vest comprising:
   a sheet rigid within the directions of the plane of the sheet, flexible to bending motion and having a shape conforming to a torso thereby forming a vest extending vertically in front from a position just below the neck to a position just above the hips and extending horizontally across the torso from positions just below the armpit and extended rearward of the torso sides terminating at portions on the rearward side of the torso;
   means adapted to receive organ interactive instrumentation to be held stably at a location on said vest relative to the organ or tissue within the torso when said vest is worn about the torso; and
   means for securing said vest to the torso and for permitting the wearer substantial freedom of movement without affecting the position relative to the organ or tissue of said means adapted to receive said instrumentation.

2. The vest of claim 1 wherein said sheet includes a plastic material.

3. The vest of claim 2 wherein said plastic is a low density polyethylene.

4. The vest of claim 1 wherein said sheet is multiply apertured to have a plurality of apertures.

5. The vest of claim 1 wherein the flexibility of said sheet is shaped to human torso contours.

6. The vest of claim 1 wherein said sheet has peripheral portions covered by a skin abrasion retardant material.

7. The vest of claim 1 wherein said vest is configured in the shape of the torso of a nonhuman animal.

8. The vest of claim 1 wherein said vest is configured in the shape of a human torso.

9. A vest for positioning medical instrumentation about the human or animal torso in a fixed position relative to a torso located organ or tissue for ambulatory torso instrumentation, said vest comprising:
   a sheet dimensionally rigid within the directions of the plane of said sheet, flexible to bending motion and having a shape conforming to a torso thereby forming a vest extending vertically in front from a position just below the neck to a position just above the hips and extending horizontally across the torso from positions just below the armpit and extended rearward of the torso sides terminating at portions on the rearward side of the torso;
   organ or tissue interactive instrumentation held stably at a location on said vest relative to the organ or tissue within the torso when said vest is worn about the torso; and
   means for securing said vest to the torso and for permitting the wearer substantial freedom of movement without affecting the position relative to the organ or tissue of said means adapted to receive said instrumentation.

10. The vest of claim 9 wherein said instrumentation includes a sensor having a radiation sensitive detector for radiation emanating from locations within said torso.

11. The vest of claim 10 wherein said sensor is positioned on said vest in a position proximate to the heart when the vest is worn about the torso, thereby to respond to radioactivity in the left ventricle of the heart.

12. The vest of claim 11 further including a high voltage power supply for energizing said sensor and means for mounting said power supply proximate to said sensor whereby high voltage lines between said power supply and said sensor are of minimal length.

13. The vest of claim 12 further including means responsive to sensed radiation from said heart for providing an output indication of heart ejection fraction.

14. The vest of claim 11 further including at least one auxiliary sensor positioned to detect background radiation in said torso when said vest is fastened about said torso.

15. The vest of claim 11 wherein said sensor includes a multiplicity of cadmium telluride radiation sensors positioned to provide sensing of radiation from the heart which is insensitive to limited motions of said sensor relative to said heart ventricle across the breast of said torso.

16. The vest of claim 14 further including means for supporting said means for providing an output indication of heart ejection fraction about the torso.

17. The vest of claim 11 wherein said sensor includes a sodium iodide crystal detector.

18. The vest of claim 9 wherein said instrumentation is selected from the group of heart function sensors consisting of radioactive decay, sonic, plethysmography, tidal lung volume, dielectric constant, ECG, EMG, ratiographic tissue absorption characteristic, and temperature sensors or combinations.

19. The vest of claim 9 wherein said adapted means is further adapted to include an array of instrumentation affixed to said sheet.

20. The vest of claim 9 wherein said adapted means is further adapted to include separate emitting and detecting instrumentation located on opposite sides of said organ or tissue.

21. The vest of claim 9 further including front located means providing quick release of said vest from said torso.

22. The vest of claim 9 wherein said instrumentation includes means for operating said vest as a tranductor.

23. The vest of claim 22 wherein said instrumentation is operative to detect torso expansion.

24. The vest of claim 9 wherein said instrumentation includes means for administering a medical treatment to said organ or tissue.

* * * * *